US008758988B2

(12) United States Patent
Jomha et al.

(10) Patent No.: US 8,758,988 B2
(45) Date of Patent: Jun. 24, 2014

(54) CRYOPRESERVATION OF ARTICULAR CARTILAGE

(75) Inventors: Nadr Mohamed Jomha, Edmonton (CA); Locksley Earl McGann, Spruce Grove (CA); Janet Anne Wade Elliott, Edmonton (CA); Garson Law, Edmonton (CA); Fraser Forbes, Edmonton (CA); Alireza Abazari Torgabeh, Edmonton (CA); Babak Maghdoori, Edmonton (CA); Andrew Weiss, Winnipeg (CA)

(73) Assignee: The Governors of the University of Alberta, Edmonton, Alberta (CA)

( * ) Notice: Subject to any disclaimer, the term of this patent is extended or adjusted under 35 U.S.C. 154(b) by 0 days.

(21) Appl. No.: 13/502,695

(22) PCT Filed: Oct. 19, 2010

(86) PCT No.: PCT/CA2010/001643
§ 371 (c)(1),
(2), (4) Date: Jul. 4, 2012

(87) PCT Pub. No.: WO2011/047469
PCT Pub. Date: Apr. 28, 2011

(65) Prior Publication Data
US 2012/0264211 A1 Oct. 18, 2012

Related U.S. Application Data

(60) Provisional application No. 61/252,923, filed on Oct. 19, 2009.

(51) Int. Cl.
*A01N 1/00* (2006.01)
(52) U.S. Cl.
USPC .............................................. 435/1.1; 435/1.2
(58) Field of Classification Search
USPC ................................................... 435/1.1, 1.2
See application file for complete search history.

(56) References Cited

U.S. PATENT DOCUMENTS

| 5,071,741 | A | * | 12/1991 | Brockbank | ..................... 435/1.3 |
| 6,740,484 | B1 | | 5/2004 | Khirabadi et al. | |
| 7,157,222 | B2 | | 1/2007 | Khirabadi et al. | |
| 8,440,390 | B2 | * | 5/2013 | Brockbank | ..................... 435/1.1 |
| 2010/0240127 | A1 | | 9/2010 | Elliott et al. | |

FOREIGN PATENT DOCUMENTS

CA 2482045 3/2006

OTHER PUBLICATIONS

Sharma et al. A Novel Method to Measure Cryoprotectant Permeation Into Intact Articular Cartilage; Cryobiology, vol. 54 (2007) pp. 196-203.*
Jomha et al. Permeation of Several Cryoprotectant Agents Into Porcine Articular Cartilage; Cryobiology, vol. 58 (Nov. 18, 2008) pp. 110-114.*
Farrant, J., et al., (1974), Optimal recovery of lymphocytes and tissue culture cells following rapid cooling, Nature, 249, 452-453.
Abrahamsen, J.F., et al., (2002), Cryopreserving human peripheral blood progenitor cells with 5-percent rather than 10-percent DMSO results in less apoptosis and necrosis in CD34+ cells, Transfusion, 42, 1573-1580.
Rubinstein R., et al., (1995), Processing and cryopreservation of placental/umbilical cord blood for unrelated bone marrow reconstitution, Proceedings of the National Academy of Sciences, USA, 92, 10119-10122.
Sharma R., et al., (2007), Abstract of a novel method to measure cryoprotectant permeation into intace atricular cartilage, Cryobiology, 54, 196-203.
Mukherjee, I.N., (2008), Cryoprotectant transport through articular cartilage for long-term storage:experiment and modeling studies, Osteoarthritis cartilage, 16, 1379-1386.
Jomha, N.M., et al., (2002), Cryopreservation of intact human articular cartilage, Journal of Orthopaedic Research, 20, 1253-1255.
Jomha, N.M., et al, (2003), Comparison of high cryoprotectant concentrations for cryopreservation of porcine articular cartilage, Cell preservation technology, 1, 201-206.
Marco, R., et al., (1992), Intact articular cartilage cryopreservation, Clinical orthopaedics and related research, 283, 11-20.
Carsi, B., et al., (2004), Cryoprotectant permeation through human articular cartilage, OsteoArthritis and Cartilage, 12, 787-792.

* cited by examiner

*Primary Examiner* — Susan Hanley
*Assistant Examiner* — Paul Martin
(74) *Attorney, Agent, or Firm* — Anthony R. Lambert

(57) ABSTRACT

The invention relates generally to methods and compositions for the cryopreservation and/or vitrification of tissue including articular cartilage and the preparation of said tissue for clinical or research use, including but not limited to joint replacement and the treatment and prevention of osteoarthritis.

20 Claims, 2 Drawing Sheets

CRYOPRESERVATION OF ARTICULAR CARTILAGE

CROSS-REFERENCE TO RELATED APPLICATIONS

This application is a 371 National Phase application of PCT/CA2010/001643 filed Oct. 19, 2010, which claims benefit of U.S. provisional application Ser. No. 61/252,923 filed Oct. 19, 2009.

FIELD

Cryopreservation of biological tissues, including articular cartilage.

BACKGROUND

There is much need for the preservation of cells and tissues, for instance, in the preservation, research and transplantation of articular cartilage or joints. Certain conditions can benefit from whole or partial joint replacement, such as osteoarthritis. Furthermore, osteochondral allografting of large joint defects (due to injury or disease) can maintain joint function and decrease the incidence of osteoarthritis. Unfortunately, the use of such procedures is limited by the availability of appropriate tissue.

Cryobiology is the study of the effects of extremely low temperatures on biological systems, with a major application being the storage of cells and tissues for research and transplantation to treat injury and disease. Cryopreservation is currently the only method available to preserve long-term function and viability of mammalian cells and tissue. Many tissue types have eluded successful cryopreservation. Currently, there are no effective cryopreservation techniques for articular cartilage (AC). Vitrification is one potential method but current processes are unsuccessful due to inadequate cryoprotectant agents (CPAs) permeation and toxicity of these CPAs.

SUMMARY

The inventors have developed a method for cryopreserving tissue, such as AC, for transplantation or research.

In an embodiment, there is provided a method for cryopreserving articular cartilage using more than one cryopreserving agent (CPA), the method comprising permeating a sample of articular cartilage with a sequence of at least two different CPAs comprising a first CPA and a second CPA, the second CPA being permeated into the sample after permeating the sample with the first CPA, to form combined CPAs having a concentration distribution within the sample, the concentration distribution of the combined CPAs being selected so that upon cooling of the sample, the combined CPAs vitrify and cryopreserve the sample. The sequence may include other CPAs, for example a total of four, five, six or seven or more CPAs. The CPAs may be selected from the group comprising dimethyl sulfoxide (D), ethylene glycol (EG), propylene glycol (PG), glycerol, (G) formamide (F), methanol (Me), ethanol (Et). Exemplary CPA sequences include D-G-PG-EG, G-EG-D-F, EG-G-D-PG, EG-G-F-D, and G-D-EG-F. Other embodiments are found in the claims, which are incorporated here by reference.

In another embodiment, there is provided a kit of compositions for use in the preservation of a sample of articular cartilage. In one embodiment said composition comprises two or more CPAs, or mixtures thereof. The kit may include instructions on how to preserve the sample.

Other features and advantages of the present invention will become apparent from the following detailed description and accompanying drawings. It should be understood, however, that the detailed description and the specific examples while indicating preferred embodiments of the invention are given by way of illustration only, since various changes and modifications of what is disclosed are intended to be covered by the claims.

BRIEF DESCRIPTION OF THE DRAWINGS

The invention will be better understood with reference to the drawings in which.

GLOSSARY

Figure 1:
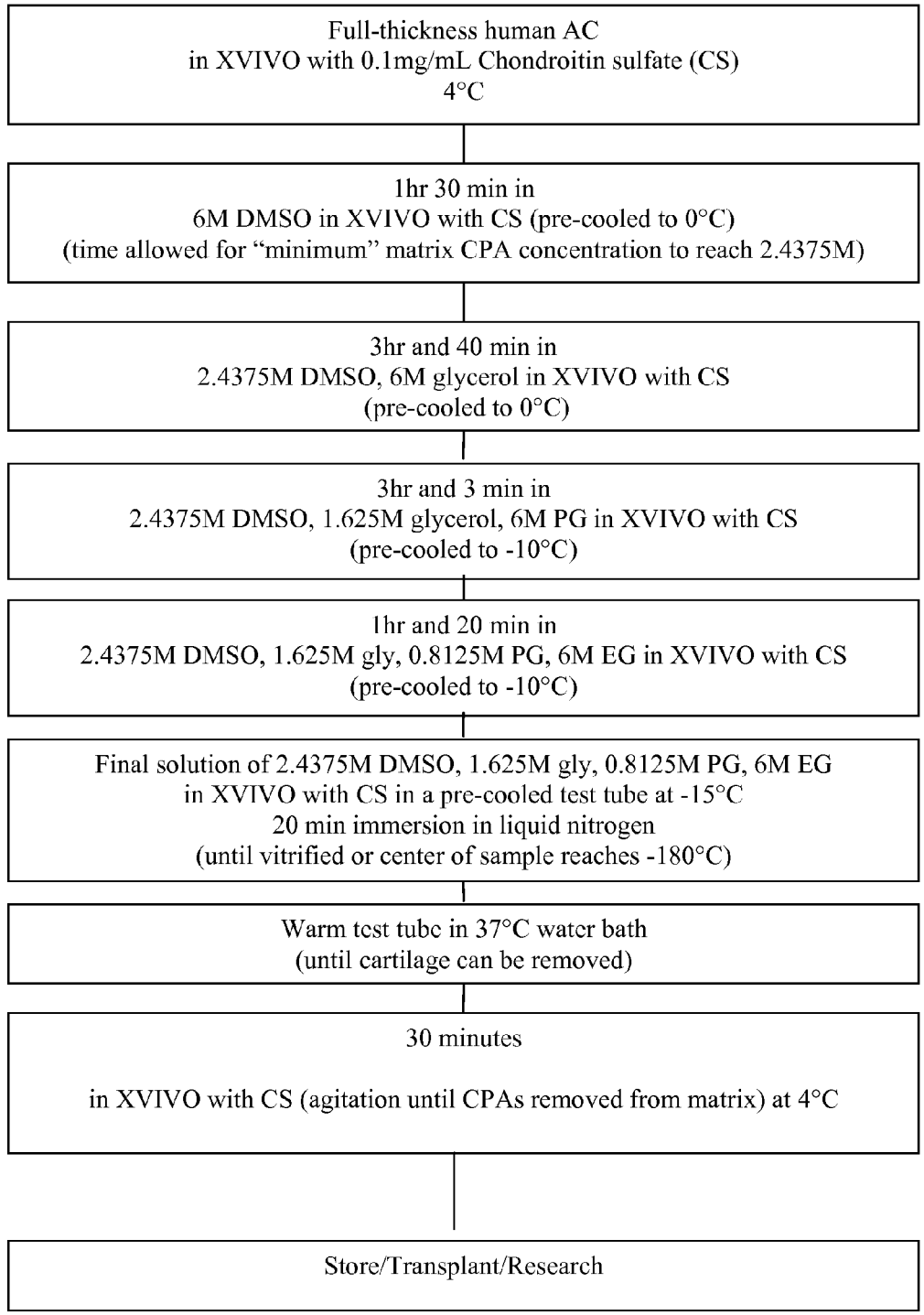
FIG. 1 is a flow chart illustrating one embodiment of a method for the cryopreservation of cartilage.

Unless defined otherwise, all technical and scientific terms used herein have the same meaning as commonly understood by one of ordinary skill in the art to which this invention belongs.

As used herein, the terms "comprising," "including," and "such as" are used in their open and non-limiting sense.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about". The term "about" means plus or minus 10%, and includes any range up to and including 10%, of the number to which reference is being made.

Further, it is to be understood that "a," "an," and "the" include the plural reference unless the content clearly dictates otherwise. For example, reference to "a compound" includes a mixture of two or more compounds. Thus, the phrase "a CPA", as used herein can also mean "one or more CPAs" or "at least one CPA" unless the context dictates otherwise.

A "beneficial effect" refers to favourable pharmacological and/or therapeutic effects, and/or improved pharmacokinetic properties and biological activity of at least one tissue, such as AC. A beneficial effect or sustained beneficial effect may manifest as decreased or no de-vitrification of tissue during the cryopreservation process and/or in desired or improved tissue or cell viability. In aspects of the invention, for instance in tissue transplantation, beneficial effects include but are not limited to decreased disease progression, decreased or alleviated disease symptoms, increased survival, or elimination or partial elimination of a condition and/or disease.

The structure of agents identified by generic or trade names herein may be taken from the standard compendium "The Merck Index"' or from databases such as PubMed, and patent databases. A person skilled in the art using these references is fully enabled to identify, manufacture and test the indications and properties in standard test models, both in vitro and in vivo.

"Condition(s) and/or disease(s)" refers to one or more pathological symptoms or syndromes for which the tissues or cells preserved herein provide a beneficial effect or therapeutic effect. Examples of conditions and/or diseases include but are not limited to osteoarthritis, tumours, avascular necrosis or traumatic joint defects.

"Vitrification" as used herein refers to the formation of an amorphous solid from an aqueous solution without significant crystal formation that usually requires a combination of high concentrations of CPAs and/or rapid cooling.

"De-vitrification" as used herein refers to the formation of ice crystals in a fluid upon re-warming from a vitrified state.

"Cryopreservation" as used herein refers to the process of cooling cells and tissues to ultra-low temperatures at which biochemical processes are significantly slowed.

Abbreviations used include dimethyl sulfoxide (DMSO; D), ethylene glycol (EG), propylene glycol (PG), glycerol (gly; G), formamide (form; F), methanol (Me), ethanol (Et), chondroitin sulphate (CS; cond sulp, cond sulf), hyaluronic acid (HA), hours (hr), minutes (min), standard deviation (std dev), average (ave; avg), molar (M).

DETAILED DESCRIPTION OF EMBODIMENTS OF THE INVENTION

There is disclosed a method for cryopreserving articular cartilage using more than one cryopreserving agent (CPA). The method comprises permeating a sample of articular cartilage with a sequence of at least two different CPAs comprising a first CPA and a second CPA, the second CPA being permeated into the sample after permeating the sample with the first CPA, to form combined CPAs having a concentration distribution within the sample, the concentration distribution of the combined CPAs being selected so that upon cooling of the sample, the combined CPAs vitrify and cryopreserve the sample. By using different CPAs permeated into the sample sequentially, a lower toxicity is obtained than would be expected for a given combination of CPAs. That is, toxicity is not additive. The sequence may include other CPAs, for example a total of four CPAs. The CPAs may be selected from the group comprising (but not limited to) dimethyl sulfoxide (D), ethylene glycol (EG), propylene glycol (PG), glycerol (G), formamide (F), methanol (Me) and ethanol (Et). Exemplary CPA sequences include D-G-PG-EG, G-EG-D-F, EG-G-D-PG, EG-G-F-D, and G-D-EG-F. Variations in cryopreservation success may still be obtained, however, due to sample differences, changes in toxicity due to temperature variation and interaction of the CPAs used. In considering the results of following the disclosed methods, sufficient success is obtained from any part of the sample surviving cryopreservation and warming since the threshold to beat is dead cartilage with no surviving chondrocytes. In the normal and expected use, the sample is typically taken from a human donor, either alive or dead. The cryopreserved sample may be used for a variety of purposes, such as study, or implantation into a different person or animal, but will not be returned to the body from which it was taken. Addition of chondroitin sulphate or hyaluronic acid to one or more of the CPAs may also be part of a cryopreservation method. Based on the examples of use of chondroitin sulphate shown below, chondroitin sulphate may be added to any or all of the solutions in an amount of, for example, from 0.1 to 10 mg/ml of the containing solution. Based on the example of use of hyaluronic acid shown below, hyaluronic acid may be added to any or all of the solutions in an amount of, for example, from 0.1 to 10 mg/ml of the containing solution. A first CPA may be permeated into tissue in combination with other CPAs provided there is a separate and subsequent permeation with at least a further CPA or combination of CPAs having a different composition than the first CPA or combination of CPAs.

In permeating the sample with a sequence of CPAs to obtain a concentration distribution of combined CPAs within a sample that permits vitrification of the combined CPAs and cryopreservation of the tissue, the CPAs should be permeated at suitable concentrations, times and temperatures. In accordance with normal cryopreservation techniques, the temperature of application of a sequence of CPAs normally does not increase from CPA to CPA but stays the same or decreases from one CPA application to another. In addition, and this would be appreciated by a person of average skill in the art, the temperature of the CPA and tissue should not be below the freezing point of the CPA or the tissue. The concentration and total time of exposure and temperature history of the CPA should be at a toxicity that is dependent on the CPA and that is not excessively toxic to the sample. CPA toxicities are known or determinable and thus application of the CPAs at a suitable toxicity is within the skill of a person of average skill in the art. The time allowed for permeation may be calculated following published permeation algorithms to achieve a level of permeation that enables vitrification of the combined CPAs and subsequent cryopreservation of the sample. In addition, methods of calculating desired permeation are also disclosed here.

The basic approach to permeating the sample of cartilage with a sequence of CPAs is to start with cartilage that has no CPA inside and put CPA 1 plus buffered saline or suitable media outside. Water and CPA then move, with the CPA permeating the cartilage, and the end result, approaching equilibrium, is that the cartilage now contains some CPA 1. Next, it is desired to add CPA 2, a different CPA from CPA 1, to the cartilage. CPA 1 should stay in the cartilage while CPA 2 is added. Hence, the CPA 2 should be added with CPA 1 at the concentration of CPA 1 already in the cartilage. The CPA 2 is added at a concentration that allows the CPA 2 to permeate the cartilage to a desired level in a reasonable amount of time without being too toxic. Thus, the preferred amount of CPA 1 present in the permeating CPA 2 solution is close to the same level as the concentration of CPA 1 already in the sample when CPA 2 is added. It is possible to have the amount of CPA 1 in the cartilage sample at the time of beginning diffusion of CPA 2 deviate from the desired final concentration, but the greater this deviation differs (higher or lower) from the desired final concentration, the more complicated the process becomes possibly without a corresponding benefit. In addition, if the CPA 1 in the cartilage is raised to a higher level than the ultimate desired concentration then the sample cartilage is exposed to unnecessarily high toxicity. A similar principle applies to the addition of any succeeding CPA, call it CPA n, where the amount of preceding CPA added with CPA n is preferably, but not always necessarily, at the concentration of the preceding CPA in the sample cartilage.

Mathematical models of freezing points may be used to determine the maximum amount that the temperature could be lowered in the next step. In one embodiment this could be calculation of the liquidus (freezing point) of the solution at the point in the tissue with the least amount of CPA. In another embodiment this could be calculation of the liquidus (freezing point) of the solution corresponding to the average amount of CPA in the tissue. In another embodiment this could be calculation of the liquidus (freezing point) of the solution corresponding to the minimum amount of CPA throughout the tissue. In one aspect the freezing point of specific solutions may be determined by any standard method such as differential scanning calorimetry (DSC) or differential thermal analysis (DTA). In another aspect the freezing point of the solution is determined by any one of a number of published models of freezing point of single or multi-solute aqueous solutions including the osmotic virial equation, or by manual determination with constant monitoring of temperature during the cooling process.

The guiding principles for arriving at a particular example of the invention include relative toxicity of CPAs at room temperature and other temperatures, computed permeation times for CPAs, computed freezing points after permeation, and a computation of whether or not a particular combination at specific concentrations will vitrify.

For example, in one embodiment, the tissue to be vitrified is added to a specific concentration of a low toxicity CPA (for example, EG) at 0° C. for a pre-specified time. After the pre-specified time (sufficient to achieve the minimum pre-specified permeation throughout the tissue), the tissue will be moved to another solution that contains two CPAs at a lower temperature (just above the freezing point of the expected starting CPA concentration within the tissue determined by a mathematical model). The determination of this second solution preferably uses combined CPAs that minimize toxicity, improve permeation, and enhance vitrification. Once again, the tissue will be left in this solution for a length of time to allow permeation to a minimum desired concentration. This can be repeated two or more times until a high enough concentration of all the different CPAs is achieved to vitrify the solution and effectively cryopreserve the tissue. In one embodiment it is repeated two times. In another embodiment it is repeated more than two times.

The method may use statistical assessment of relative toxicity of CPAs and/or mathematical models of permeation kinetics to determine parameters of addition/dilution of multiple CPAs in a step-wise manner at progressively lower temperatures resulting in progressively higher CPA concentrations until a sufficient concentration to vitrify is achieved. Exposure times can be mathematically determined for specific tissue thickness to optimize permeation while minimizing toxicity. In one aspect, the individual CPAs are added at different temperatures so that the ratios of the CPA concentrations changes throughout the protocol.

In a further embodiment, a method for cryopreserving articular cartilage using more than one cryopreserving agent comprises:
  (i) obtaining an articular cartilage sample;
  (ii) adding one CPA first at a temperature above the freezing point of the native tissue and CPA bathing solution for a sufficient period of time to obtain a desired degree of CPA tissue permeation;
  (iii) moving the tissue to another solution that contains at least one or more CPAs at the same or lower temperature then the temperature in step "(ii)", but higher than the freezing point of the solution and tissue in step (ii), for a sufficient period of time to obtain a desired degree of CPA tissue permeation;
  (iv) repeating step (iii) with different CPAs at the same or lower temperatures than previously used but higher than the solution and tissue freezing point, until a high enough concentration of all the different CPAs in the tissue is achieved to vitrify the solution and effectively cryopreserve the tissue. In one embodiment, step (iii) is repeated two times. In another embodiment, step (iii) is repeated more than two times.

In one embodiment, the articular cartilage sample is obtained from any mammal including but not limited to humans, preferably human. It is noted that skeletally mature pig knee joints are slightly smaller than human knee joints but that the cartilage thickness is similar between the two, so for this reason, it is considered to be one of the best models for cartilage transplantation procedures. It is noted that persons skilled in the art are familiar with various transplantation techniques, for instance a suitable osteochondral allografting surgical technique.

The thickness of the articular cartilage sample may be 1-6 mm, above 1 mm, or between 2 to 6 mm for example. The toxicity of the CPA may be determined by membrane integrity assays of slices taken from whole dowels post treatment or from published data for example. A dual stain technique may be used whereby intact cells will fluoresce a green colour while those with damaged membranes will fluoresce a red colour as described below. In one aspect, CPAs of similar toxicity could be administered in combination. In one aspect, they have different permeation kinetics, in another aspect they have similar permeation kinetics.

In one embodiment, the CPAs may be added in order of increasing toxicity. In another embodiment the CPAs applied subsequently to the first CPA have similar toxicity and can be administered in combination. In another embodiment, the CPAs may be administered based on permeation kinetics.

In one embodiment, certain CPAs may interact and result in different toxicity or permeation kinetics than if administered alone or administered without any subsequent or previous tissue treatment with other CPAs or compounds.

In one embodiment, the sufficient time for tissue permeation, is the time for sufficient permeation to obtain vitrification but no or minimal de-vitrification. In another embodiment it is full permeation of the tissue with the respective CPA or CPA solution.

In one method the relative toxicity of a CPA or combination thereof is determined by administering the CPA to a tissue sample or individual cells and then determining cell or tissue viability using known techniques, such as cell staining with Syto 13 and ethidium bromide, wherein intact cells are green and disrupted cells are red. The degree of cell viability can be obtained by counting the respective cells over a specified area. This can be done over various different time points and at different temperatures. Other methods include assessment of metabolic activity using a test such as WST-1 that measures mitochondrial activity.

In one method permeation kinetics of a CPA or combination thereof are determined by measurement of the amount of CPA that has diffused into a known quantity of tissue after specified periods of time and at specific temperatures. Another method would be to use magnetic resonance imaging.

The degree of success of the vitrification or cryopreservation technique can be assessed by determining cell or tissue viability as previously described from a portion of the tissue sample to be used or a control sample. Positive and negative controls or both can be used. The degree of any de-vitrification can be observed visually (e.g. formation of ice crystals upon rewarming) by loss of glass clarity and the formation of cracks.

The disclosed methods may be used for preparing cryopreserved tissue for clinical or research use. In one embodiment, said use includes a step or steps for removing CPA from the tissue to a minimized toxicity level. In one embodiment, it involves removing all or essentially all of the CPA from the tissue, in preparation for research or transplantation. In another embodiment, there is provided a method for warming the tissue to the desired temperature for use. In one embodiment, the said methods used preferably obtain the desired degree of tissue or cell viability for the intended use.

There is also provided a kit comprising one or more solutions containing in each solution one or more CPAs and optionally instructions for vitrification of tissue. A kit may comprise a package which houses a container which contains a composition of CPAs and also houses instructions for cryopreserving the tissue or articular cartilage as per the method of the invention. In one embodiment, the instructions further include instructions for preparing the tissue or articular cartilage for transplantation or research. Associated with such container(s) can be various written materials such as instructions for use, or a notice in the form prescribed by a governmental agency regulating the labelling, manufacture, use or sale of such products, which notice reflects approval by the agency of manufacture, use, or sale for human administration. Parts of a kit may be used simultaneously or chronologically staggered, i.e., at different points in time and with equal or different time intervals for any component of a kit. Time intervals can be selected to obtain the desired effect. The kit may include instructions for temperature of use of each part of the kit.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Toxicity of CPAs: DMSO, EG, PG, Glycerol, Formamide

The following methods A and B describe examples for measuring toxicity.

A. Full-thickness articular cartilage samples are stored in Dulbecco's phosphate buffered saline (PBS) solution (pH=7.0) (Gibco, BRL, MD) at 4° C. Slices of 70 μm thickness are removed using a Vibratome® (The Vibratome Company, St. Louis, Mo.) cutting from the articular surface to the bone-cartilage junction. The 70 μm thickness is sufficient to allow rapid CPA equilibration throughout the sample.

One control solution of 1×PBS and four experimental solutions of 1M, 3M, 5M, and 6M DMSO (Fisher; 99.9% pure; wt/vol) in 1×PBS are prepared. Individual samples are randomly assigned to one of five solutions and one of three temperatures (4° C., 22° C., or 37° C.) with multiple replicates. Slices are taken from each sample and immersed in 4 ml of one of the assigned solutions and temperatures in a multiwell tissue culture plate (Corning Inc., Corning, N.Y.) for various lengths of time (ranging from 0.5 min to 120 min).

Once the appropriate experimental time has elapsed, the slices are removed from their respective solution and rinsed with 1×PBS. Each slice is stained using membrane integrity dyes of Syto 13 (Molecular Probes, Eugene, Oreg.) and ethidium bromide (EB; Sigma, St. Louis, Mo.) [0.1% EB with 0.45% Syto mixed in PBS (vol/vol)] and viewed under a Leitz Dialux 22 fluorescence (440-480 nm) microscope (Leica Microsystems, Richmond Hill, ON) at 125× magnification (10× objective and 12.5× eyepiece). Two representative images from each sample are recorded by digital camera (Pixera DiRactor, Pixera Corporation, Los Gatos, Calif.) and stored on computer for later analysis. The images are then analyzed with a custom cell counting program (Viability 3.1, The Great Canadina Computer Company, Spruce Grove AB) that utilizes minimum pixel intensity to approximate the numbers of green (intact) cells and red (disrupted) cells. The cell viability (ratio of intact cells to total cells) in individual slices is normalized against the cell viability or the total number of cells in control slices maintained in 1×PBS. This is repeated in at least triplicate.

In order to confirm the results of the membrane integrity assay, a second viability assay is utilized. The assay measures the reduction of the tetrazolium salt WST-1 by mitochondrial dehydrogenases in viable cells. After exposure to the control solution of 1×PBS or the four experimental solutions of 1M, 3M, 5M and 6M DMSO, 10 slices are randomly immersed in 2 ml of one of the five solutions in a 24-well tissue culture plate (Costar #3526, Corning Inc., Corning, N.Y.) for various lengths of time (ranging from 0 min to 120 min) at 22° C. Once the appropriate experimental time has elapsed, the slices of AC are removed from their respective solution and immersed in 2 ml of 1×PBS in another 24-well tissue culture plate for 10 minutes to allow for CPA removal. The slices are then placed in another 24-well plate with each well containing 200 μl of appropriate growth media and 30 μl of WST-1 cell proliferation reagent (Roche Diagnostics, Indianapolis, Ind.). The plates are incubated at 37° C. in 5% $CO_2$ for 24 hours. A 100 μl aliquot of media from each well is transferred to a 96-well flat-bottom plate (Costar #3595, Corning Inc., Corning, N.Y.) and absorbency is measured at 450 nm using a SpectraMax Plus 384™ microplate spectrophotometer (Molecular Devices, Sunnyvale, Calif.).

Media and WST-1 reagent are incubated in parallel with samples. The resultant spectrophotometer readings are subtracted from readings for treated samples to eliminate background effects. Spectrophotometer readings are normalized against pooled control samples incubated in 1×PBS over the same period. All samples are repeated at least in triplicate.

B. Cells from the tissue samples are isolated by digesting the surrounding matrix. For example, for articular cartilage, the tissue is placed in a 100 mm diameter petri dish containing 1× Dulbecco's phosphate buffered saline solution (pH 7.0) (PBS, Gibco, BRL, MD). The PBS is removed and 20 mL of Dubelcco's modified eagle media with F-12 nutritional supplement and 1% penicillin-streptomycin (DMEM/F-12, Gibco, BRL, MD) containing 1 mg/mL of collagenase 1A (Sigma-Aldrich Canada, Oakville, ON,) is added. The cartilage is incubated with shaking at 37° C. and 5% $CO_2$ for 6 hours and then the solution is passed through a 40 μm nylon cell strainer (BD biosciences, Mississauga, ON). The solution is centrifuged at 500 rcf for 6 minutes to pellet the chondrocytes; they are washed once in PBS, and then plated on the first 7 rows of 96-well clear tissue culture treated microplates (Costar, Corning Inc Life Sciences, Lowell, Ma) at 25,000 cells per well in 1004 DMEM/F-12 with 10% fetal bovine serum (FBS, Gibco, BRL, MD). After leaving the plates at room temperature for 30 minutes to allow the chondrocytes to settle they are incubated at 37° C. and 5% $CO_2$ for 36-48 hours to allow the chondrocytes to attach to the plates and recover from the stress of the collagenase digestion. Half of the supernatant is removed from each well using a 96-well pipetting device (vacupette, Bel-Art products, Pequannock, N.J.); 1004 of DMEM/F-12 with 10% FBS (DMEM/F-12/FBS) is added and removed from each well using a vacupette to wash the cells. 100 μL of DMEM/F-12/FBS is added to the positive control wells and to the blank wells (FIG. 1) and 100 μL of pure dimethyl sulfoxide (DMSO, Fisher, Fair lawn, NJ) is added to the negative control wells.

Increasing concentrations of each CPA are added to individual wells until the desired concentration is reached. Each addition is calculated to limit osmotic expansion/contraction of the cell to less than 40% of its original volume to prevent overexpansion/contraction cell lysis. After each addition, three minutes are allowed to pass to permit full equilibration prior to the next higher concentration of that solution.

After the desired concentration of CPA is achieved, the plates are incubated at 37° C. and 5% $CO_2$ for one of 5, 20, 60 or 120 minutes. At the end of the incubation 1004 of solution is removed from all wells and replaced with 100 μL of DMEM/F-12/FBS; this solution is allowed to equilibrate for 3 minutes then 100 μL of solution is again removed and replaced to achieve a slower dilution of CPA and prevent osmotic induced cell damage. This solution is allowed to equilibrate for 3 minutes; then the wells are emptied. 100 μL of WST-1 (Roche diagnostics, Laval, QC) in solution (10 μL WST-1:100 μL phenol red free DMEM/F-12/FBS) is added to each well of the plate and the plate is incubated at 37° C. and 5% $CO_2$ for 90 minutes. The absorbance of the solutions in each well is measured using a spectrophotometer (Spectra-Max Plus 384, Molecular devices, Sunnyvale, Calif.) reading at 450 nm using 650 nm as a background reference. The wells are again emptied and 40 μL of SYTO 13 (Invitrogen, Eugene, Or)(1.7%)/ethidium bromide (0.34%) is added and left protected from light for 30 minutes. The fluorescence of each well is measured using a fluorometer (SpectraMax Gemini EM, Molecular devices, Sunnyvale, Calif.) (excitation 460/emission 510(Syto13); excitation 490/emission 610 (EB)). Images from representative wells are captured using a 40 times magnification inverted fluorescent microscope (Eclipse TE 2000-U, Nikon Canada Inc, Mississauga, ON), the images analysed using a custom cell counting program (Viability 3.1, The Great Canadian Computer Company, Spruce Grove, AB) and used to standardise cell number and viability readings from the fluorometric data.

Permeation Kinetics of CPAs in AC Matrix

Full thickness AC (on 5-10 mm bone base) is harvested from the sample tissue using a hand-held coring device and held at 4° C. in 1× Dulbecco's phosphate-buffered saline (PBS) solution (pH 7.1) (Gibco Invitrogen, Carlsbad, Calif.). Each osteochondral dowel (OCD) is assigned to one of four CPA treatment groups [DMSO, PG, EG, glycerol (all at 6.5M, in 1×PBS)] and one of 11 incubation times (1 second, 1, 2, 5, 10, 15, 30, 60, 120, 180 minutes, 24 hours), as well as one of three temperatures (4, 22, 37° C.). Each combination of treatment, time, and temperature is repeated at least three times.

The tissue sample is isolated by scalpel and the tissue returned to 1×PBS for 5 min, then blotted lightly using Kimwipes® tissue (Kimberly-Clark, Roswell, Ga.) to remove excess fluid from the sample surface, weighed (W1), and immediately immersed in 5 ml of CPA solution for the specified incubation time at the specified temperature. After incubation, the sample is removed from the solution, blotted lightly and weighed for a second time (W2). The sample is then placed into a 35×10 mm cell culture dish (Corning Inc., Corning, N.Y.) containing 4 mL of 1×PBS, fully immersed in the PBS and the dish sealed with Parafilm® (American National Can, Chicago, Ill.) and held for 24 h at 22° C. under dark conditions to allow the CPA within the AC disc to fully equilibrate with the surrounding PBS solution. After 24 h, the CPA/PBS solution is mixed using a pipettor and a 1 mL sample is taken into a 1.5 mL microcentrifuge tube (Thermo Fisher Scientific, Waltham, Mass.). From this sample, 50 μL is placed into a μOSMETTE™ micro-osmometer (Precision Systems, Natick, Mass.) to determine its osmolality (Osm).

Calculations

As the measured osmolalities are quite low, the immersion solution can be considered ideal and dilute.

The number of moles of CPA in the surrounding solution is calculated as:

$$n_s(\text{mole}) = \frac{(\pi_s - \pi_{PBS})(mosm/kg) \times 4 \text{ mL} \times 0.99770(g/mL)}{1000(mosm/osm) \times 1000(g/kg)} \quad (1)$$

where $\pi_S$=osmolality of the final solution, $\pi_{PBS}$=osmolality of the initial PBS solution, and 0.99770=density of water at 22° C.

The total number of moles of CPA that had permeated into the sample is then given by:

$$n_{total}(\text{mole}) = n_S(\text{mole}) + n_{inside\ cartilage}(\text{mole}) \quad (2)$$

Note: $n_{inside\ cartilage}$ was estimated to be negligible and has been omitted from the calculations.

The weight of the CPA is calculated as:

$$Wt_{CPA}(g) = n_{total}(\text{mole}) \times MW_{CPA}\left(\frac{g}{\text{mole}}\right) \quad (3)$$

where $MW_{CPA}$ is the molar mass of the CPA.

The volume of CPA was then calculated as:

$$V_{CPA}(\text{mL}) = \frac{Wt_{CPA}(g)}{Density_{CPA}\left(\frac{g}{\text{mL}}\right)} \quad (4)$$

Note: True (pure) densities for each CPA at corresponding temperatures may be obtained from the literature or a commercial simulation package such as Aspen-HYSYS v. 2004.2.

The amount of water within isotonic cartilage is measured to be 77.6±0.5% (S.E.) by mass in a previous study. Assuming a constant dry weight percentage of 22.4%, the dry weight of each AC disc is calculated as:

$$\text{Dry Weight}(g) = W1(g) \times 0.224 \quad (5)$$

The volume of water in the sample after 24 h equilibration in 1×PBS is calculated as:

$$V_{water\ in\ treated\ cartilage}(\text{mL}) = \frac{W2(g) - [\text{Dry Weight}(g) + Wt_{CPA}(g)]}{1\left(\frac{g}{\text{mL}}\right)} \quad (6)$$

Finally, the concentration of CPA that penetrated the AC disc was calculated to be:

$$[CPA]\left(\frac{\text{mol}}{L}\right) = \frac{n_{total}(\text{mole}) \times 1000\left(\frac{\text{ml}}{L}\right)}{V_{CPA}(\text{mL}) + V_{water\ in\ treated\ cartilage}(\text{mL})} \quad (7)$$

Note that this is the solution concentration (i.e. moles per fluid volume in sample and not moles per sample volume).

Exposure Time Determination

The exposure time in each experiment was determined based on the physical understanding of the CPA diffusion in cartilage gained from the triphasic model by Abazari et al. (A biomechanical triphasic approach to the transport of nondilute solutions in articular cartilage. Author(s): Abazari A, Elliott JAW, Law G K, McGann L E, Jomha N M. Source: BIOPHYSICAL JOURNAL Volume: 97 Issue: 12 Pages: 3054-3064 Published: DEC 16 2009):

That there exists a time-dependent spatial distribution of the CPA within the cartilage during CPA diffusion.

That the minimum CPA concentration in this setup (i.e. for cryopreservation of cartilage on the bone) is always at the bone-cartilage interface.

That using the average value for the CPA concentration in cartilage as the target for permeation can result in partial loss of the cells due to freezing of half of the cartilage near the bone due to inadequate concentration of the CPA there, and that the diffusion time of the CPA in each step of the experiments is preferably determined such that the minimum concentration, not the average concentration, reaches the required concentration for each step.

That Fick's law of diffusion always overestimates the diffusion time of the CPA in cartilage compared to the biomechanical model. Therefore, using Fick's law for the calculation of the diffusion times ensures that the minimum required concentration in the cartilage is reached.

Based on the above-mentioned understandings, permeation times of the CPA in cartilage were calculated using predictions of Fick's law for the one-dimensional diffusion of each CPA in cartilage:

$$\frac{\partial C_{CPA}}{\partial t} = -D \frac{\partial C_{CPA}}{\partial x^2} \quad (8)$$

The values of the diffusion coefficients for the single CPA diffusion in water were used in the calculations. The values of the diffusion coefficients were calculated before, by fitting Fick's law to the experimental data, as explained in the preceding section of this patent labeled "Permeation Kinetics of CPAs in AC matrix".

The initial concentration was set to zero, i.e., $C_{CPA}(x, t=0)=0$, and the average initial thickness was THK=2 mm.

The boundary conditions, for the cartilage on bone, were $$\frac{\partial C_{CPA}}{\partial x} = 0$$

at x=0, and $C_{CPA}=C^*$ at x=THK, where $C^*$ is the concentration of the CPA in the external bath at each step of the protocol.

The temperature dependence of the diffusion coefficients was calculated by fitting an Arrhenius equation to the values of diffusion coefficients obtained for each CPA at 3 different temperatures as in the preceding section of this patent labeled "Permeation Kinetics of CPAs in AC matrix". The activation energies, Ea, for the 4 CPAs (D, EG, PG and G) are tabulated in Table (1). The values of diffusion coefficients were taken from Jomha et al (N M Jomha, G K Law, A Abazari, K Rekieh, J A W Elliott, L E McGann. Permeation of several cryoprotectant agents into porcine articular cartilage. Cryobiology 58(1), 110-114, 2009). For F (formamide), 2 values for diffusion coefficients of formamide in water at 2 different temperatures were extracted from the literature:

| Temperature (K) | Diffusion coefficient (m²/s) | Reference |
| --- | --- | --- |
| 278.2 | $0.95 \times 10^{-9}$ | [1] |
| 298.15 | $1.58 \times 10^{-9}$ | [2] |

[1] Albright JG, Gosting LJ. The diffusion coefficient of formamide in dilute aqueous solutions at 25° as measured with the gouy diffusiometer *J. Phys. Chem.*, 1960, 64 (10), pp 1537-1539.
[2] Easteal AJ, Woolf LA. Pressure and temperature dependence of tracer diffusion coefficients of methanol, ethanol, acetonitrile, and formamide in water, *J. Phys. Chem.*, 1985, 89 (7), pp 1066-1069)

Then, these values were fitted to an Arrhenius equation to calculate the constant and activation energy for formamide. Those values are also tabulated in Table (1). As an example, the increase in the minimum DMSO concentration in cartilage, diffusing from a bath of 3 M DMSO solution, at −10° C., was calculated by solving Eqn. (8) as the following:

First, the diffusion coefficient of DMSO in water at −10° C. was calculated from the results of the Arrhenius fit in Table (1).

$$D_{DMSO}(\text{at } T=-10° \text{C.}=263 \text{K})=298.95\times10^{-9}\times\exp(-3.9/0.001986/263)=1.71\times10^{-10} \text{m}^2/\text{s}$$

Eqn. (8) was solved using COMSOL Multiphysics® with initial and boundary conditions as previously mentioned, and the value of minimum concentration, i.e. $C_{CPA}$ at x=0, was plotted versus time as in FIG. 2).

Figure 2:
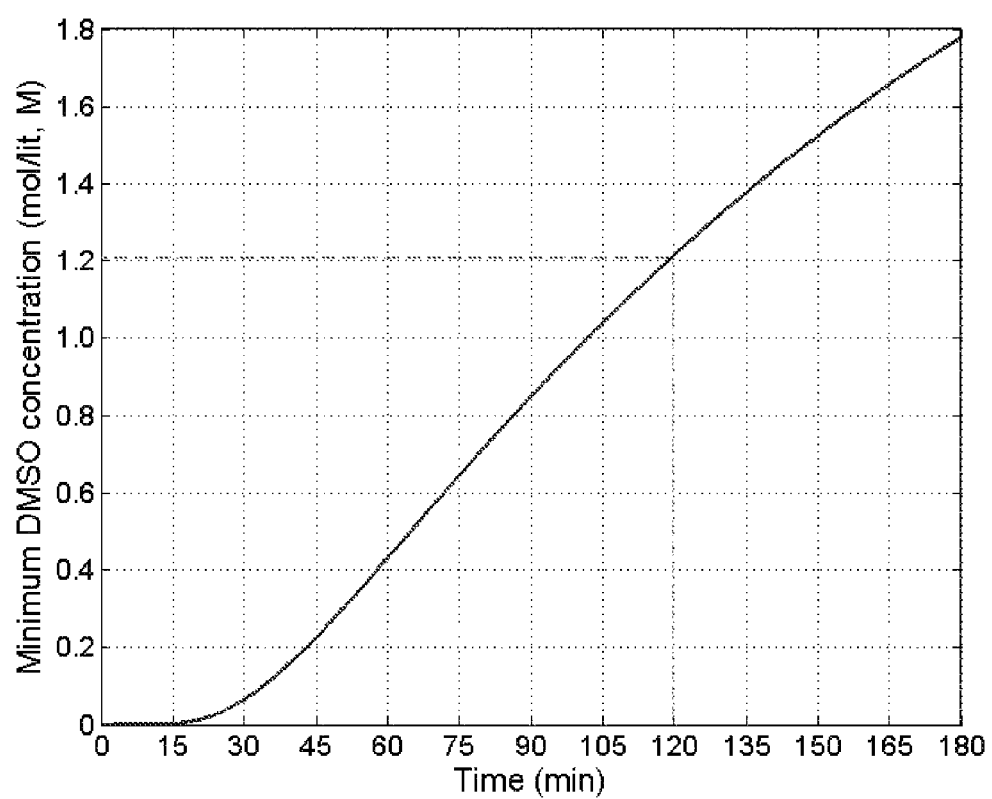
FIG. 2 is a graph showing the increase in minimum cartilage DMSO concentration (minimum located at the bone-cartilage interface) in cartilage with 2 mm thickness with DMSO concentration of 3 M in the external bath for 180 minutes.

From FIG. 2, the minimum concentration of DMSO in cartilage can be found at any time. Therefore, for example, if a minimum concentration of 1.2 M is desired in one step at −10° C. with DMSO concentration of 3 M in the external bath, the cartilage must be immersed in the bath for 120 minutes.

TABLE (1)

The activation energies and constants obtained for 5 CPAs by fitting the results from the preceding section of this patent labeled "Permeation Kinetics of CPAs in AC matrix" and literature data with an Arrhenius equation.

$$D_{cw} = D_{cwo} \times \exp\left(-\frac{E_a}{RT}\right)$$

| | | |
| --- | --- | --- |
| D (DMSO) | $D_{cwo}$ (×10⁻⁹ m²/s) | 298.95 |
| | $E_a$ (Kcal/mol) | 3.9 |
| E (EG) | $D_{cwo}$ (×10⁻⁹ m²/s) | 183.30 |
| | $E_a$ (Kcal/mol) | 3.8 |
| P (PG) | $D_{cwo}$ (×10⁻⁹ m²/s) | 16971.0 |
| | $E_a$ (Kcal/mol) | 6.63 |
| G (Gly) | $D_{cwo}$ (×10⁻⁹ m²/s) | 208.03 |
| | $E_a$ (Kcal/mol) | 5.6 |
| F (Form) | $D_{cwo}$ (×10⁻⁹ m²/s) | 1903.510 |
| | $E_a$ (Kcal/mol) | 4.198 |

R = 0.001986 Kcal/(mol. K), T in degrees K

EXAMPLE 1

Vitrification Protocol

A full-thickness articular cartilage dowel was removed from the distal end of the femur and placed in XVIVO at 4° C. with 0.1 mg/mL chondroitin sulphate. All subsequent solutions contained 0.1 mg/mL chondroitin sulphate. The dowel was then placed in 40 mL of 6M dimethyl sulphoxide (DMSO, pre-cooled to 0° C.) and incubated for 1 hr 30 min to achieve a "minimum" concentration of 2.438M DMSO within the cartilage matrix. The dowel was then removed, quickly blotted, and incubated in a solution containing 2.4375M DMSO and 6M glycerol (pre-cooled to 0° C.) for 3 hr and 40 min. to achieve minimum concentrations of 2.4375M DMSO and 1.625M glycerol within the matrix. Again, the dowel was removed, blotted, and incubated in a solution (pre-cooled to −10° C.) containing 2.4375M DMSO, 1.625M glycerol, and 6M propylene glycol (PG) for 3 hr and 3 min. to achieve minimum concentrations of 2.4375M DMSO, 1.625M glycerol, and 0.8125M PG. The dowel was removed, blotted, and incubated in a solution (pre-cooled to −15° C.) containing 2.4375M DMSO, 1.625M glycerol, 0.8125M PG and 6M EG for 1 hr and 20 min giving final matrix minimum concentrations of 2.4375M DMSO, 1.625M glycerol, 0.8125M PG and 1.625M EG. The dowel in this solution was then plunged into liquid nitrogen for 20 min to achieve vitrification of the cryoprotectant solution and cryopreservation of the tissue. Another sample was held in liquid nitrogen for 3 months. To evaluate the resultant effectiveness of this vitrification procedure, the tube was re-warmed in a water bath at 37° C. until the dowel could be removed. The dowel was then placed in 150 mL of XVIVO for 30 min at 4° C., with gentle agitation to remove the CPAs from the cartilage matrix. Full-thickness slices were then taken and stained with fluorescent dyes SYTO-13/Ethidium bromide and cell membrane integrity was assessed.

All solutions were made in XVIVO and contained 0.1 mg/mL chondroitin sulphate. All times were pre-determined based on permeation kinetics for each CPA using 2 mm as the estimated cartilage thickness. FIG. 1 is a flow-chart illustrating one embodiment on how the method used in this example can be used to vitrify the AC for subsequent transplantation.

In one example, of a method, a full thickness (approximately 2 mm thick) 10 mm diameter dowel of human articular cartilage was permeated, vitrified and warmed using the described solution: (1) 2.4375 DMSO, (2) 1.625M glycerol, (3) 0.8125M PG and (4) 1.625M EG with each CPA added at progressively lower temperatures. Subsequent staining with Syto 13 and ethidium bromide highlighted intact and disrupted cells. Manual counting of cells recorded approximately 77% intact cell recovery in this human tissue after the vitrification procedure repeated on nine different knee arthroplasty samples held for 20 min in liquid nitrogen (Table 2k) and one human cadaveric donor (3 repeats) resulted in 83% recovery (Table 2l). In the sample held for 3 months, the cell recovery was approximately 73%.

EXAMPLE 2

Vitrification Protocol

A full-thickness articular cartilage dowel was removed from the distal end of the femur and placed in XVIVO at 4° C. without chondroitin sulphate. The permeation times were calculated to provide a "minimum" concentration within the matrix. The same procedure as above was followed with the following solution exposures:

6M glycerol for 3 hr and 40 min at 0° C., 1.625M glycerol and 6M DMSO for 1 hr and 27 min at 0° C., 1.625M glycerol, 1.625M DMSO and 6M formamide for 50 min at −10° C., and 1.625M gly, 1.625M DMSO, 1.625M formamide and 6M EG for 1 hr 18 min at −15° C. to give a final concentration of 1.625M glycerol, 1.625M DMSO, 1.625M formamide, and 1.625M EG within the cartilage matrix. All solutions were made in XVIVO. The test tube was then plunged into liquid nitrogen for 20 min to achieve vitrification of the cryoprotectant solution and cryopreservation of the sample. The samples were warmed as above. The cell recovery determined by membrane integrity stains was approximately 60% based on two independent samples (Table 2q).

The same procedure was completed with permeation times calculated to provide an "average" concentration within the matrix resulting in the following procedure:

6M glycerol for 3 hr at 0° C., 1.625M glycerol and 6M DMSO for 2 hr at 0° C., 1.625M glycerol, 1.625M DMSO and 6M formamide for 1 hr at 0° C., and 1.625M gly, 1.625M DMSO, 1.625M formamide and 6M EG for 1 hr 30 min at −10° C. to give a final concentration of 1.625M glycerol, 1.625M DMSO, 1.625M formamide, and 1.625M EG within the cartilage matrix. The test tube was then plunged into liquid nitrogen for 20 min to achieve vitrification of the cryoprotectant solution and cryopreservation of the sample. The samples were warmed as above. The cell recovery determined by membrane integrity stains was approximately 44% based on three samples (Table 2p).

EXAMPLE 3

Vitrification Protocol

A full-thickness articular cartilage dowel was removed from the distal end of the femur and placed in XVIVO at 4° C. with 0.1 mg/mL chondroitin sulphate. The same procedure as above was followed with the following solution exposures:

6M glycerol for 3 hr 40 min at 0° C., 1.625M glycerol and 6M EG for 2 hr 32 min at 0° C., 1.625M glycerol, 2.4375M EG and 6M DMSO for 1 hr 42 min at −10° C., 1.625M gly, 2.4375M EG, 1.625M DMSO and 6M form for 53 min at −15° C. to give a final concentration of 1.625M gly, 2.4375M EG, 1.625M DMSO and 0.8125M form within the cartilage matrix. The test tube was then plunged into liquid nitrogen for 20 min to achieve vitrification of the cryoprotectant solution and cryopreservation of the sample. The samples were warmed as above. The cell recovery determined by membrane integrity stains was approximately 48% based on seven independent samples (Table 2u).

EXAMPLE 4

Sample Vitrification Protocols and Results

The following tables demonstrate a variety of different combinations of CPAs using different numbers of CPAs, in varying order and with different exposure times and different concentration end points (i.e. "minimum" or "average" permeation concentrations). Chondroitin sulphate (0.1 mg/mL) was added to only those solutions where stated. In those stated protocols, the chondroitin sulphate was added to all solutions used with the exception of the initial solution following cartilage harvest in the operating room. The following tables combine data obtained from human cadaveric donors (denoted by "CTC") and cartilage removed from knee joints during total knee arthroplasty surgical procedures (denoted by "TKA"). In addition UAH denotes a sample from the University of Alberta Hospital while M is denotes a sample from the Misericordia Hospital (Edmonton).

TABLE 2a

D-G-PG (8M):
Permeation times calculated for "average" concentration throughout the matrix.
6M DMSO for 40 min at 0° C.
3M DMSO, 6M gly for 65 min at −7° C.
3M DMSO, 2M gly, 6M PG for 4 h at −15° C.
Final concentration = 3M DMSO, 2M gly, 3M PG.

| Treatment | Location | Recovery (%) | Age | Sex | Source | Date | Trial |
|---|---|---|---|---|---|---|---|
| D-G-PG (8M) | Femoral | 43 | 19 | Female | CTC donor | Oct. 2, 2007 | 45 |
| | Tibial | 14 | 19 | Female | CTC donor | Oct. 2, 2007 +1 | 45 |
| | Femoral | 4.97 | 76 | Female | TKA14 | Jan. 28, 2010 | 65 |
| | Femoral | 8.91 | 69 | Male | TKA 15 | Jan. 28, 2010 | 65 |
| | Femoral | 15.27 | 79 | Female | UAH16 | Jan. 28, 2010 | 65 |
| | Avg | 17.23 | | | | | |

TABLE 2b

G-EG-D (8M):
Permeation times calculated for "minimum" concentration throughout the matrix.
6M gly for 5 h at 0° C.
2.67M gly, 6M EG for 2 h at 0° C.
2.67M gly, 2.67M EG, 6M DMSO for 2 h at −10° C.
Final concentration = 2.67M gly, 2.67M EG, 2.67M DMSO.

| Treatment | Location | Recovery (%) | Age | Sex | Source | Date | Trial |
|---|---|---|---|---|---|---|---|
| G-EG-D (8M) | Femoral | 28 | 49 | Male | CTC donor | Sep. 2, 2009 | 61 |
| | Femoral | 17.98 | 60 | Female | TKA9 | Jan. 13, 2010 | 65 |
| | Femoral | 1.66 | 59 | Female | TKA12 | Jan. 15, 2010 | 65 |
| | Femoral | 15.65 | 77 | Female | TKA13 | Jan. 15, 2010 | 65 |
| | Avg | 15.82 | | | | | |

TABLE 2c

G-D-F (8M):
Permeation times calculated for "minimum" concentration throughout the matrix.
6M gly for 4 h at 0° C.
2.67M gly, 6M DMSO for 2 h at 0° C.
2.67M gly, 2.67M DMSO, 6M F for 2 h at −10° C.
Final concentration = 2.67M gly, 2.67M DMSO, 2.67M F.

| Treatment | Location | Recovery (%) | Age | Sex | Source | Date | Trial |
|---|---|---|---|---|---|---|---|
| G-D-F (8M) | Femoral | 36.12 | 76 | Female | TKA14 | Jan. 28, 2010 | 65 |

TABLE 2d

G-EG-F (8M):
Permeation times calculated for "minimum" concentration throughout the matrix.
6M gly for 4 h at 0° C.
2.67M gly, 6M EG for 2 h at 0° C.
2.67M gly, 2.67M EG, 6M formamide for 2 h at −10° C.
Final concentration = 2.67M gly, 2.67M EG, 2.67M F.

| Treatment | Location | Recovery (%) | Age | Sex | Source | Date | Trial |
|---|---|---|---|---|---|---|---|
| G-EG-F (8M) | Femoral | 33 | 17 | Male | CTC31 | Nov. 5, 2009 | x |
| | Femoral | 41 | 17 | Male | CTC31 | Nov. 5, 2009 | x |
| | Femoral | 0.25 | 49 | Male | CTC1 | Dec. 9, 2009 | 65 |
| | Femoral | 0.8 | 49 | Male | CTC1 | Dec. 9, 2009 | 65 |
| | Femoral | 1.44 | 59 | Female | TKA11 | Jan. 15, 2010 | 65 |
| | Femoral | 2.08 | 59 | Female | TKA12 | Jan. 15, 2010 | 65 |
| | Femoral | 0.68 | 77 | Female | TKA13 | Jan. 15, 2010 | 65 |
| | Avg | 11.32 | | | | | |

TABLE 2e

D-G-PG-EG (8M):
Permeation times calculated for "average" concentration throughout the matrix.
6M DMSO for 40 min at 0° C.
3M DMSO, 6M gly for 65 min at −7° C.
3M DMSO, 2M gly, 6M PG for 30 min at −15° C.
3M DMSO, 2M gly, 1M PG, 6M EG for 35 min at −15° C.
3M DMSO, 2M gly, 1M PG, 2M EG for 2 h at −15° C.
Final concentration = 3M DMSO, 2M gly, 1M PG, 2M EG.

| Treatment | Location | Recovery (%) | Age | Sex | Source | Date | Trial |
|---|---|---|---|---|---|---|---|
| D-G-PG-EG (8M) | Femoral | 52 | 19 | Female | CTC donor | Oct. 2, 2007 | 45 |
|  | Femoral | 30 | 19 | Female | CTC donor | Oct. 2, 2007 | 45 |
|  | Femoral | 27 | 17 | Male | CTC31 | Nov. 5, 2009 | x |
|  | Femoral | 33 | 17 | Male | CTC31 | Nov. 5, 2009 | x |
|  | Femoral | 3 | 49 | Male | CTC1 | Dec. 9, 2009 | 65 |
|  | Femoral | 3 | 49 | Male | CTC1 | Dec. 9, 2009 | 65 |
|  | Femoral | 38.76 | 64 | Female | TKA1 | Nov. 26, 2009 | 65 |
|  | Femoral | 24.48 | 76 | Female | TKA2 | Nov. 26, 2009 | 65 |
|  | Femoral | 11.23 | 68 | Male | TKA3 | Nov. 26, 2009 | 65 |
|  | Avg | 24.7 |  |  |  |  |  |

TABLE 2f

G-EG-F-D-PG:
Permeation times calculated for "minimum" concentration within matrix for gly and
EG and "average" concentration throughout the matrix for F, DMSO, and PG.
6M gly for 4 h at 0° C.
2.67M gly, 6M EG for 3 h at 0° C.
2M gly, 2M EG, 6M formamide for 30 min at −10° C.
2M gly, 2M EG, 1.5M formamide, 6M DMSO for 30 min at −10° C.
2M gly, 2M EG, 1.5M formamide, 1.25M DMSO, 6M PG for 30 min at −10° C.
Final concentration = 2M gly, 2M EG, 1.5M formamide, 1.25M DMSO, 1.25M PG.

| Treatment | Location | Recovery (%) | Age | Sex | Source | Date | Trial |
|---|---|---|---|---|---|---|---|
| G-EG-F-DG-P | Femoral | 2 | 17 | Male | CTC31 | Nov. 5, 2009 | x |

TABLE 2g

G-EG-F-D-PG-Me—Et:
Permeation times calculated for "minimum" concentration
within the matrix for G, EG, F, and methanol and "average"
concentration throughout the matrix for DMSO, ethanol and PG
6M gly for 4 h at 0° C.
2.67M gly, 6M EG for 3 h at 0° C.
2.67M gly, 2.67M EG, 6M formamide for 20 min at −10° C.
2M gly, 2M EG, 0.4M formamide, 6M DMSO for 20 min at −10° C.
2M gly, 2M EG, 0.4M formamide, 0.4M DMSO, 6M PG for 20 min at −10° C.
2M gly, 2M EG, 0.4M formamide, 0.4M DMSO, 0.4M PG, 6M methanol for 20 min at −10° C.
2M gly, 2M EG, 0.4M formamide, 0.4M DMSO, 0.4M PG, 0.4M methanol, 6M ethanol
for 20 min at −10° C.
Final concentration = 2M gly, 2M EG, 0.4M formamide, 0.4M DMSO, 0.5M PG, 0.4M
methanol, 2.3M ethanol.

| Treatment | Location | Recovery (%) | Age | Sex | Source | Date | Trial |
|---|---|---|---|---|---|---|---|
| G-EG-F-D-PG-Me—Et | Femoral | 28 | 17 | Male | CTC31 | Nov. 5, 2009 | x |
|  | Femoral | 74.36 | 52 | Female | TKA8 | Jan. 13, 2010 | 65 |
|  | Femoral | 11.99 | 60 | Female | TKA9 | Jan. 13, 2010 | 65 |
|  | Femoral | 33.52 | 76 | Female | TKA14 | Jan. 28, 2010 | 65 |
|  | Femoral | 4.98 | 69 | Male | TKA15 | Jan. 28, 2010 | 65 |
|  | Femoral | 3.16 | 79 | Female | UAH16 | Jan. 28, 2010 | 65 |
|  | Avg | 26 |  |  |  |  |  |

TABLE 2h

G-EG-F-D-PG-Me—Et:
Permeation times calculated for "minimum" concentration within the matrix for G, EG, F, methanol and "average" concentration throughout the matrix for DMSO, PG, and ethanol.
6M gly for 4 h at 0° C.
2.67M gly, 6M EG for 3 h at 0° C.
1.5M gly, 1.5M EG, 6M formamide for 20 min at −10° C.
1.5M gly, 1.5M EG, 0.8M formamide, 6M DMSO for 20 min at −10° C.
1.5M gly, 1.5M EG, 0.8M formamide, 0.8M DMSO, 6M PG for 20 min at −10° C.
1.5M gly, 1.5M EG, 0.8M formamide, 0.8M DMSO, 0.8M PG, 6M methanol for 20 min at −10° C.
1.5M gly, 1.5M EG, 0.8M formamide, 0.8M DMSO, 0.8M PG, 0.8M methanol, 6M ethanol for 20 min at −10° C.
Final concentration = 1.5M gly, 1.5M EG, 0.8M formamide, 0.8M DMSO, 0.62M PG, 0.8M methanol, 2.3M ethanol.

| Treatment | Location | Recovery (%) | Age | Sex | Source | Date | Trial |
|---|---|---|---|---|---|---|---|
| G-EG-F-D-PG-Me—Et | Femoral | 5.24 | 52 | Female | TKA8 | Jan. 13, 2010 | 65 |
|  | Femoral | 14.45 | 60 | Female | TKA9 | Jan. 13, 2010 | 65 |
|  | Avg | 9.85 |  |  |  |  |  |

Further experimentation pursued specific combinations of CPAs including a 4 component solution consisting of DMSO (D), Glycerol (G), propylene glycol (PG) and ethylene glycol (EG) in a 3:2:1:2 ratio for a total concentration of 6.5M. The permeation times were based on an "average" concentration within the matrix and included:

TABLE 2i

6M DMSO for 30 min at 0° C.
2.4375M DMSO and 6M gly for 45 min at 0° C.
2.4375M DMSO, 1.625M gly and 6M PG for 20 min at −5° C.
2.4375M DMSO, 1.625M gly, 0.8125M PG and 6M EG for 25 min at −10° C.
For a final solution of 2.4375M DMSO, 1.625M gly, 0.8125M PG, and 1.625M EG. Three different samples were trialed with an average of 37% recovery.

| sample | treatment | Chon Sulf | recovery | avg | std dev |
|---|---|---|---|---|---|
| 1 | 6.5 D-G-PG-EG | 0 | 10.8 |  |  |
| 2a | 6.5 D-G-PG-EG | 0 | 25.9 |  |  |
| 2b | 6.5 D-G-PG-EG | 0 | 74.1 | 36.9 | 33.1 |

This was repeated using exposure times to reach a calculated "minimum" concentration of each CPA within the matrix. The process included:
  6M DMSO for 1 hr 30 min at 0° C.
  2.4375M DMSO and 6M gly for 3 h 40 min at 0° C.
  2.4375M DMSO, 1.625M gly and 6M PG for 3 h 3 min at −10° C.
  2.4375M DMSO, 1.625M gly, 0.8125M PG and 6M EG for 1 h 20 min at −15° C.
The final solution consisted of 2.4375M DMSO, 1.625M gly, 0.8125M PG, and 1.625M EG. There was approximately 49% cell recovery in 7 samples from 5 different patients.

TABLE 2j

| sample | treatment | Chon Sulf | recovery | avg | std dev |
|---|---|---|---|---|---|
| 1 | 6.5 D-G-PG-EG | 0 | 45.2 |  |  |
| 2 | 6.5 D-G-PG-EG | 0 | 47.4 |  |  |
| 3a | 6.5 D-G-PG-EG | 0 | 73.9 |  |  |
| 3b | 6.5 D-G-PG-EG | 0 | 61.8 |  |  |
| 4a | 6.5 D-G-PG-EG | 0 | 38.7 |  |  |
| 5 | 6.5 D-G-PG-EG | 0 | 49.2 |  |  |
| 4b | 6.5 D-G-PG-EG | 0 | 29.4 | 49.4 | 14.7 |

The same process was followed with the addition of 0.1 mg/mL chondroitin sulphate with approximately 77% cell recovery from 14 samples from 8 different patients.

TABLE 2k

| sample | treatment | Chon Sulf | recovery | avg | std dev |
|---|---|---|---|---|---|
| 1a | 6.5 D-G-PG-EG | 0.1 | 88.26 |  |  |
| 1b | 6.5 D-G-PG-EG | 0.1 | 48.15 |  |  |
| 2 | 6.5 D-G-PG-EG | 0.1 | 81.04 |  |  |
| 3a | 6.5 D-G-PG-EG | 0.1 | 89.08 |  |  |
| 3b | 6.5 D-G-PG-EG | 0.1 | 86.14 |  |  |
| 3c | 6.5 D-G-PG-EG | 0.1 | 76.9 |  |  |
| 4a | 6.5 D-G-PG-EG | 0.1 | 77.72 |  |  |
| 4b | 6.5 D-G-PG-EG | 0.1 | 81.25 |  |  |
| 5 | 6.5 D-G-PG-EG | 0.1 | 71.19 |  |  |
| 6a | 6.5 D-G-PG-EG | 0.1 | 81.16 |  |  |
| 6b | 6.5 D-G-PG-EG | 0.1 | 53.06 |  |  |
| 7a | 6.5 D-G-PG-EG | 0.1 | 86.998 |  |  |
| 7c | 6.5 D-G-PG-EG | 0.1 | 81.18 |  |  |
| 8 | 6.5 D-G-PG-EG | 0.1 | 74.47 | 76.9 | 12.3 |

All of the following solutions had permeation times calculated based on "minimum" concentrations throughout the matrix unless otherwise stated.

The previous results (Table 2k) were obtained using cartilage discarded during total knee replacement surgery. We repeated the same experiment with normal articular cartilage from one young normal donor using 3 separate 10 mm diameter cores from the same subject with approximately 84% cell recovery.

TABLE 2l

| sample | treatment | Chon Sulf | recovery | avg | std dev |
|---|---|---|---|---|---|
| 4a-CTC | 6.5 D-G-PG-EG | 0.1 | 76.1 | | |
| 4b-CTC | 6.5 D-G-PG-EG | 0.1 | 91.4 | | |
| 4c-CTC | 6.5 D-G-PG-EG | 0.1 | 84.1 | 83.9 | 7.7 |

A pellet culture was performed to ensure the cells were indeed viable and a pellet did form indicating the ability for these cells to produce a matrix and the cells were able to produce glycosaminoglycans (a product of normal chondrocytes).

TABLE 2m

| DNA (pg) | gag (µg) | gag/DNA |
|---|---|---|
| 11096 | 8.28 | 745.80 |
| 6415 | 7.89 | 1229.47 |
| 13436 | 8.97 | 667.94 |

Another method to vitrify cartilage included a re-ordering of the CPAs (without chondroitin sulphate) and included:
  6M EG for 1 h 28 min at 0° C.
  1.625M EG and 6M gly for 3 h 37 min at 0° C.
  1.625M EG, 1.625M gly and 6M DMSO for 2 h 0 min at −10° C.
  1.625M EG, 1.625M gly, 2.4375M DMSO and 6M PG for 3 h 58 min at −15° C.
Resulting in a final solution of 1.625M EG, 1.625M gly, 2.4375M DMSO and 0.8125M PG with a recovery rate of approximately 40%.

TABLE 2n

| sample | treatment | Chon Sulf | recovery | avg | std dev |
|---|---|---|---|---|---|
| 1a | 6.5 EG-G-D-PG | 0 | 46.98 | | |
| 1b | 6.5 EG-G-D-PG | 0 | 48.9 | | |
| 2a | 6.5 EG-G-D-PG | 0 | 23.2 | | |
| 4a | 6.5 EG-G-D-PG | 0 | 38.8 | | |
| 4b | 6.5 EG-G-D-PG | 0 | 43.4 | 40.3 | 10.3 |

Another variation was to alter the concentrations of CPA from the 3:2:1:2 that was used with D-G-PG-EG (without chondroitin sulphate). Thus the exposures were:
  6M DMSO for 1 h 2 min at 0° C.
  1.5M DMSO and 6M gly for 4 h 13 min at 0° C.
  1.5M DMSO, 2M gly and 6M PG for 3 h 37 min at −10° C.
  1.5M DMSO, 2M gly, 1M PG and 6M EG for 2 h 32 min at −15° C.
For a final solution containing 1.5M DMSO, 2M gly, 1M PG, and 2M EG that resulted in approximately 46% cell recovery after vitrification and warming.

TABLE 2o

| sample | Treatment | Chon Sulf | recovery | avg | std dev |
|---|---|---|---|---|---|
| 1a | 6.5 D-G-PG-EG | 0 | 60.3 | | |
| 1b | 6.5 D-G-PG-EG | 0 | 40.2 | | |
| 2 | 6.5 D-G-PG-EG | 0 | 36.2 | | |
| 3 | 6.5 D-G-PG-EG | 0 | 47.5 | 46.1 | 10.6 |

Another four combination CPA solution included glycerol, DMSO, formamide and EG without chondroitin sulphate. This process used the "average" permeation calculations for the CPA exposure times. This solution included:
  6M glycerol for 3 h at 0° C.
  1.625M gly and 6M DMSO for 2 h at 0° C.
  1.625M gly, 1.625M DMSO and 6M formamide for 1 h at 0° C.
  1.625M gly, 1.625M DMSO, 1.625M form and 6M EG for 1 h 30 min at −10° C.
The final solution of 1.625M gly, 1.625M DMSO, 1.625M form and 1.625M EG resulted in approximately 44% cell recovery.

TABLE 2p

| sample | treatment | Chon Sulf | recovery | avg | std dev |
|---|---|---|---|---|---|
| 1 | 6.5 G-D-F-EG | 0 | 31.9 | | |
| 2 | 6.5 G-D-F-EG | 0 | 0.6 | | |
| 3 | 6.5 G-D-F-EG | 0 | 99.2 | 43.9 | 50.4 |

We then performed the same experiment but using the "minimum" permeation calculation and the solution included:
  6M glycerol for 3 h 40 min at 0° C.
  1.625M gly and 6M DMSO for 1 h 27 min at 0° C.
  1.625M gly, 1.625M DMSO and 6M formamide for 50 min at −10° C.
  1.625M gly, 1.625M DMSO, 1.625M form and 6M EG for 1 h 18 min at −15° C.
The final solution of 1.625M gly, 1.625M DMSO, 1.625M form and 1.625M EG resulted in approximately 60% cell recovery.

TABLE 2q

| sample | treatment | Chon Sulf | recovery | avg | std dev |
|---|---|---|---|---|---|
| 1 | 6.5 G-D-F-EG | 0 | 47.8 | | |
| 2 | 6.5 G-D-F-EG | 0 | 71.4 | 59.6 | 16.7 |

When the same solution had 0.1 mg/mL chondroitin sulphate added with the same exposure times, the results decreased to approximately 22%.

TABLE 2r

| sample | treatment | Chon Sulf | recovery | avg | std dev |
|---|---|---|---|---|---|
| 1a | 6.5 G-D-F-EG | 0 | 26.2 | | |
| 1b | 6.5 G-D-F-EG | 0 | 4.9 | | |
| 2a | 6.5 G-D-F-EG | 0 | 12.5 | | |
| 2b | 6.5 G-D-F-EG | 0 | 31 | | |
| 3a | 6.5 G-D-F-EG | 0 | 28 | | |
| 3b | 6.5 G-D-F-EG | 0 | 32 | | |
| 4 | 6.5 G-D-F-EG | 0 | 16.6 | | |
| 5 | 6.5 G-D-F-EG | | 21 | 21.5 | 11.9 |

Another reordering of the relevant CPAs was performed and the solution included:
  6M EG for 1 h 28 min at 0° C.
  1.625M EG and 6M gly for 3 h 37 min at 0° C.
  1.625M EG, 1.625M gly and 6M form for 50 min at −10° C.
  1.625M EG, 1.625M gly, 1.625M form and 6M DMSO for 1 h 42 min at −15° C.

The final solution of 1.625M EG, 1.625M gly, 1.625M form and 1.625M DMSO resulted in approximately 16% cell recovery after vitrification.

TABLE 2s

| sample | treatment | Chon Sulf | recovery | avg | std dev |
|---|---|---|---|---|---|
| 1 | 6.5 EG-G-F-D | 0 | 6.3 | | |
| 2 | 6.5 EG-G-F-D | 0 | 33.9 | | |
| 3a | 6.5 EG-G-F-D | 0 | 18.1 | | |
| 3b | 6.5 EG-G-F-D | 0 | 4 | 15.6 | 13.7 |

Another reordering resulted in:
  6M EG for 1 h 28 min at 0° C.
  1.625M EG and 6M gly for 3 h 37 min at 0° C.
  1.625M EG, 1.625M gly and 6M DMSO for 1 h 32 min at −10° C.
  1.625M EG, 1.625M gly, 1.625M DMSO and 6M form for 53 min at −15° C.

The final solution of 1.625M EG, 1.625M gly, 1.625M DMSO and 1.625M form resulted in approximately 22% cell recovery after vitrification.

TABLE 2t

| sample | treatment | Chon Sulf | recovery | avg | std dev |
|---|---|---|---|---|---|
| 1 | 6.5 EG-G-D-F | 0 | 6.8 | | |
| 2 | 6.5 EG-G-D-F | 0 | 9.9 | | |
| 3a | 6.5 EG-G-D-F | 0 | 21.6 | | |
| 3b | 6.5 EG-G-D-F | 0 | 32 | | |
| 4 | 6.5 EG-G-D-F | 0 | 12.5 | | |
| 5a | 6.5 EG-G-D-F | 0 | 32.8 | | |
| 5b | 6.5 EG-G-D-F | 0 | 35 | 21.5 | 11.9 |

TABLE 2u

| sample | treatment | Chon Sulf | recovery | avg | std dev |
|---|---|---|---|---|---|
| 1 | 6.5 G-EG-D-F | 0.1 | 55.7 | | |
| 2 | 6.5 G-EG-D-F | 0.1 | 64.3 | | |
| 3 | 6.5 G-EG-D-F | 0.1 | 59.0 | | |
| 4a | 6.5 G-EG-D-F | 0.1 | 24.9 | | |
| 4b | 6.5 G-EG-D-F | 0.1 | 9.7 | | |
| 4c | 6.5 G-EG-D-F | 0.1 | 30.2 | | |
| 5a | 6.5 G-EG-D-F | 0.1 | 111.8 | | |
| 5b | 6.5 G-EG-D-F | 0.1 | 39.2 | | |
| 5c | 6.5 G-EG-D-F | 0.1 | 39.5 | | |
| 6a | 6.5 G-EG-D-F | 0.1 | 58.9 | | |
| 6b | 6.5 G-EG-D-F | 0.1 | 61 | | |
| 6c | 6.5 G-EG-D-F | 0.1 | 53 | | |
| 7a | 6.5 G-EG-D-F | 0.1 | 39.5 | | |
| 7b | 6.5 G-EG-D-F | 0.1 | 23.8 | | |
| 7c | 6.5 G-EG-D-F | 0.1 | 55.1 | 48.4 | 23.9 |

Another solution consisted of DMSO, gly, EG and formamide with chondroitin sulphate added:

6M DMSO for 1 h 30 min at 0 C
  2.4375M DMSO, 6M gly for 3 h 40 min at 0° C.
  2.4375M DMSO, 1.625M gly, 6M EG for 1 h 53 min at −10 C
  2.4375M DMSO, 1.625M gly, 1.625M EG, 6M formamide for 53 min at −15 C for a final concentration of 2.4375M DMSO, 1.625M gly, 1.625M EG, and 0.8125M formamide resulting in 53% cell recovery.

TABLE 2v

| Treatment | Location | Recovery (%) | Age | Sex | Source | Date | Trial |
|---|---|---|---|---|---|---|---|
| D-G-EG-F (6.5M) | Femoral | 53.2 | 69 | Male | Mis15a | Oct. 13, 2010 | 69 |

One more vitrification protocol using 4 CPAs at a 2:3:2:1 ratio and chondroitin sulphate included:
  6M gly for 3 h 40 min at 0° C.
  1.625M gly and 6M EG for 2 h 32 min at 0° C.
  1.625M gly, 2.4375M EG and 6M DMSO for 1 h 42 min at −10° C.
  1.625M gly, 2.4375M EG, 1.625M DMSO and 6M form for 53 min at −15° C.

The final solution contained 1.625M gly, 2.4375M EG, 1.625M DMSO and 0.8125M form and resulted in approximately 48% cell recovery after vitrification and warming.

One more solution contained DMSO, gly, PG, and EG with the addition of 1 mg/mL hyaluronic acid:
  6M DMSO for 1 h 30 min at 0 C
  2.4375M DMSO, 6M gly for 3 h 40 min at 0 C
  2.4375M DMSO, 1.625M gly, 6M PG for 3 h 3 min at −10 C
  2.4375M DMSO, 1.625M gly, 0.8125M PG, 6M EG for 1 h 20 min at −15 C for a final concentration of 2.4375M DMSO, 1.625M gly, 0.8125M EG, 1.625M EG resulting in 39% cell recovery.

TABLE 2w

| Treatment | Location | Recovery (%) | Age | Sex | Source | Date | Trial |
|---|---|---|---|---|---|---|---|
| D-G-PG-EG- (6.5M) | Femoral | 39.2 | 69 | Male | Mis15b | Oct. 13, 2010 | 69 |

Further experimental solutions were examined as described below:

D-G-PG-EG (6.5M):

Permeation times calculated for "average" concentration throughout the matrix.

6M DMSO for 33 min at 0° C.
2.4375M DMSO, 6M gly for 45 min at 0° C.
2.4375M DMSO, 1.625M gly, 6M PG for 20 min at −5 C
2.4375M DMSO, 1.625M gly, 0.8125M PG, 6M EG for 25 min at −10 C Final concentration=2.4375M DMSO, 1.625M gly, 0.8125M PG, 1.625M EG.

TABLE 2x

| | In PBS solution | | | | | | |
|---|---|---|---|---|---|---|---|
| Treatment | Location | Recovery (%) | Age | Sex | Source | Date | Trial |
| D-G-PG-EG (6.5M) | Femoral | 2.35 | 62 | Male | TKA6 | Mar. 25, 2010 | 67 |
| | Femoral | 9.08 | 56 | Male | TKA22 | Apr. 22, 2010 | 67 |
| | Femoral | 19.69 | 62 | Male | UAH33d | May 12, 2010 | 67 |
| | Avg | 10.37 | | | | | |

TABLE 2y

| | In XVIVO solution | | | | | | |
|---|---|---|---|---|---|---|---|
| Treatment | Location | Recovery (%) | Age | Sex | Source | Date | Trial |
| D-G-PG-EG (6.5M) | Femoral | 65.12 | 73 | Male | TKA17b | Apr. 15, 2010 | 67 |
| | Femoral | 37.59 | 55 | Male | TKA27c | Apr. 30, 2010 | 67 |
| | Femoral | 54.46 | 57 | Female | TKA31a | May 07, 2010 | 67 |
| | Avg | 52.39 | | | | | |

D-G-PG-EG (8M):

Permeation times calculated for "average" concentration throughout the matrix.

6M DMSO for 40 min at 0 C
3M DMSO, 6M gly for 1 h 5 min at −7 C
3M DMSO, 2M gly, 6M PG for 30 min at −15 C
3M DMSO, 2M gly, 1M PG, 6M EG for 1 h 35 min at −15 C Final concentration=3M DMSO, 3M gly, 1M PG, 2M EG.

TABLE 2z

| | In PBS solution | | | | | | |
|---|---|---|---|---|---|---|---|
| Treatment | Location | Recovery (%) | Age | Sex | Source | Date | Trial |
| D-G-PG-EG (8M) | Femoral | 17.02 | 51 | Male | TKA1 | Mar. 19, 2010 | 67 |
| | Femoral | 12.46 | 39 | Female | TKA2 | Mar. 25, 2010 | 67 |
| | Femoral | 65.13 | 61 | Male | UAH25 | Apr. 29, 2010 | 67 |
| | Femoral | 69.61 | 62 | Male | UAH33c | May 12, 2010 | 67 |
| | Avg | 41.05 | | | | | |

TABLE 2aa

| | In X-VIVO solution | | | | | | |
|---|---|---|---|---|---|---|---|
| Treatment | Location | Recovery (%) | Age | Sex | Source | Date | Trial |
| D-G-PG-EG (8M) | Femoral | 11.96 | 57 | Female | TKA7 | Mar. 31, 2010 | 67 |
| | Femoral | 80.15 | 74 | Male | TKA28 | Apr. 30, 2010 | 67 |
| | Femoral | 58.38 | 62 | Male | UAH33g | May 12, 2010 | 67 |
| | Avg | 50.16 | | | | | |

G-D-F (6.5M):
Permeation times calculated for "minimum" concentration throughout the matrix.
6M gly for 3 h 30 min at 0° C.
2.167M gly, 6M DMSO for 2 h 30 min at 0° C.
2.167M gly, 2.167M DMSO, 6M F for 1 h 30 min at −10° C.
Final concentration=2.167M gly, 2.167M DMSO, 2.167M F.

TABLE 2bb

| | In PBS solution | | | | | | |
|---|---|---|---|---|---|---|---|
| Treatment | Location | Recovery (%) | Age | Sex | Source | Date | Trial |
| G-D-F (6.5M) | Femoral | 26.16 | 51 | Female | TKA14 | Apr. 08, 2010 | 67 |
| | Femoral | 30.80 | 65 | Female | TKA18b | Apr. 15, 2010 | 67 |
| | Femoral | 19.94 | 62 | Male | UAH33e | May 12, 2010 | 67 |
| | Avg | 25.63 | | | | | |

TABLE 2cc

| | In X-VIVO solution | | | | | |
|---|---|---|---|---|---|---|
| Treatment | Location | Recovery (%) | Age | Sex | Source | Date |
| G-D-F (6.5M) | Femoral | 83.39 | 72 | Female | TKA12 | Apr. 01, 2010 |
| | Femoral | 52.92 | 58 | Male | UAH19 | Apr. 15, 2010 |
| | Femoral | 16.09 | 62 | Male | UAH33f | May 12, 2010 |
| | Avg | 50.80 | | | | |

G-D-F (8M):
Permeation times calculated for "minimum" concentration throughout the matrix.
6M gly for 4 h at 0° C.
2.67M gly, 6M DMSO for 3 h at 0° C.
2.67M gly, 2.67M DMSO, 6M F for 2 h at −10° C.
Final concentration=2.67M gly, 2.67M DMSO, 2.67M F.

TABLE 2dd

| | In PBS solution | | | | | | |
|---|---|---|---|---|---|---|---|
| Treatment | Location | Recovery (%) | Age | Sex | Source | Date | Trial |
| G-D-F (8M) | Femoral | 5.35 | 64 | Female | UAH15 | Apr. 08, 2010 | 67 |
| | Femoral | 8.09 | 78 | Male | UAH24 | Apr. 29, 2010 | 67 |
| | Femoral | 66.29 | 62 | Male | UAH33a | May 12, 2010 | 67 |
| | Avg | 26.58 | | | | | |

TABLE 2ee

| | In X-VIVO solution | | | | | | |
|---|---|---|---|---|---|---|---|
| Treatment | Location | Recovery (%) | Age | Sex | Source | Date | Trial |
| G-D-F (8M) | Femoral | 39.34 | 66 | Male | TKA13 | Apr. 07, 2010 | 67 |
| | Femoral | 4.96 | 59 | Female | TKA21 | Apr. 22, 2010 | 67 |
| | Femoral | 68.08 | 67 | Male | TKA35b | May 14, 2010 | 67 |
| | Avg | 37.46 | | | | | |

G-D-F-EG (6.5M):
Permeation times calculated for "minimum" concentration throughout the matrix.
6M gly for 3 h at 0° C.

1.625M gly, 6M DMSO for 2 h at 0° C.

1.625M gly, 1.625M DMSO, 6M F for 1 h at 0° C.

1.625M gly, 1.625M DMSO, 1.625M F, 6M EG for 1 h 30 min at −10° C.
Final concentration=1.625M gly, 1.625M DMSO, 1.625M F, 1.625M EG.

TABLE 2ff

| | In PBS solution | | | | | | |
|---|---|---|---|---|---|---|---|
| Treatment | Location | Recovery (%) | Age | Sex | Source | Date | Trial |
| G-D-F-EG (6.5M) | Femoral | 86.86 | 59 | Male | TKA11 | Apr. 01, 2010 | 67 |
| | Femoral | 21.51 | 85 | Female | UAH26a | Apr. 29, 2010 | 67 |
| | Femoral | 52.70 | 64 | Female | TKA29c | May 06, 2010 | 67 |
| | Avg | 53.69 | | | | | |

TABLE 2gg

| | In X-VIVO solution | | | | | | |
|---|---|---|---|---|---|---|---|
| Treatment | Location | Recovery (%) | Age | Sex | Source | Date | Trial |
| G-D-F-EG (6.5M) | Femoral | 60.77 | 70 | Female | TKA4 | Mar. 25, 2010 | 67 |
| | Femoral | 0.93 | 67 | Female | TKA23 | Apr. 29, 2010 | 67 |
| | Femoral | 92.00 | 85 | Female | UAH32b | May 10, 2010 | 67 |
| | Avg | 51.23 | | | | | |

G-D-F-EG (8M):
Permeation times calculated for "minimum" concentration throughout the matrix.
6M gly for 4 h at 0° C.
2M gly, 6M DMSO for 3 h at 0° C.
2M gly, 2M DMSO, 6M F for 2 h at −10° C.
2M gly, 2M DMSO, 2M F, 6M EG for 2 h at −10° C.
Final concentration=2M gly, 2M DMSO, 2M F, 2M EG.

TABLE 2hh

| | In PBS solution | | | | | | |
|---|---|---|---|---|---|---|---|
| Treatment | Location | Recovery (%) | Age | Sex | Source | Date | Trial |
| G-D-F-EG (8M) | Femoral | 32.91 | 59 | Male | TKA3 | Mar. 25, 2010 | 67 |
| | Femoral | 41.95 | 64 | Female | TKA29b | May 06, 2010 | 67 |
| | Femoral | 25.84 | 57 | Female | TKA31b | May 07, 2010 | 67 |
| | Avg | 33.57 | | | | | |

TABLE 2ii

| | In X-VIVO solution | | | | | | |
|---|---|---|---|---|---|---|---|
| Treatment | Location | Recovery (%) | Age | Sex | Source | Date | Trial |
| G-D-F-EG (8M) | Femoral | 56.48 | 73 | Male | TKA17a | Apr. 15, 2010 | 67 |
| | Femoral | 49.09 | 73 | Male | TKA17a | Apr. 15, 2010 | 67 |
| | Femoral | 24.99 | 85 | Female | UAH32a | May 10, 2010 | 67 |
| | Avg | 43.52 | | | | | |

Final concentration=2M gly, 2M EG, 0.5M formamide, 0.54M DMSO, 0.5M PG, 0.5M methanol, 2.3M ethanol.

G-EG-F-D-PG-Me-Et:

Permeation times calculated for "minimum" concentration within the matrix for G, EG, F and methanol with "average" concentration throughout the matrix for DMSO, ethanol and PG.

6M gly for 3 h 30 min at 0° C.
2M gly, 6M EG for 2 h 30 min at 0° C.
2M gly, 2M EG, 6M formamide for 20 min at −10° C.
2M gly, 2M EG, 0.5M formamide, 6M DMSO for 20 min at −10° C.
2M gly, 2M EG, 0.5M formamide, 0.5M DMSO, 6M PG for 20 min at −10° C.
2M gly, 2M EG, 0.5M formamide, 0.5M DMSO, 0.5M PG, 6M methanol for 20 min at −10° C.
2M gly, 2M EG, 0.5M formamide, 0.5M DMSO, 0.5M PG, 0.5M methanol, 6M ethanol for 20 min at −10° C.

TABLE 2jj

| | In PBS solution | | | | | | |
|---|---|---|---|---|---|---|---|
| Treatment | Location | Recovery (%) | Age | Sex | Source | Date | Trial |
| G-EG-F-D-PG-Me—Et | Femoral | 18.89 | 62 | Male | TKA9 | Mar. 31, 2010 | 67 |
| | Femoral | 75.50 | 65 | Female | TKA18a | Apr. 15, 2010 | 67 |
| | Femoral | 15.91 | 62 | Male | UAH33h | May 12, 2010 | 67 |
| | Avg | 34.30 | | | | | |

TABLE 2kk

| | In X-VIVO solution | | | | | | |
|---|---|---|---|---|---|---|---|
| Treatment | Location | Recovery (%) | Age | Sex | Source | Date | Trial |
| G-EG-F-D-PG-Me—Et | Femoral | 54.31 | 77 | Male | TKA16 | Apr. 09, 2010 | 67 |
| | Femoral | 76.02 | 85 | Female | UAH26b | Apr. 29, 2010 | 67 |
| | Femoral | 30.47 | 62 | Male | UAH33b | May 12, 2010 | 67 |
| | Avg | 48.02 | | | | | |

G-EG-F-D-PG-Me-Et:

Permeation times calculated for "minimum" concentration within the matrix for G, EG, F and methanol with "average" concentration throughout the matrix for DMSO, ethanol and PG.

6M gly for 4 h at 0° C.
2.46M gly, 6M EG for 3 h at 0° C.
2.46M gly, 2.46M EG, 6M formamide for 20 min at −10° C.
2.46M gly, 2.46M EG, 0.615M formamide, 6M DMSO for 20 min at −10° C.
2.46M gly, 2.46M EG, 0.615M formamide, 0.615M DMSO, 6M PG for 20 min at −10° C.
2.46M gly, 2.46M EG, 0.615M formamide, 0.615M DMSO, 0.615M PG, 6M methanol for 20 min at −10° C.
2.46M gly, 2.46M EG, 0.615M formamide, 0.615M DMSO, 0.615M PG, 0.615M methanol, 6M ethanol for 20 min at −10° C.

Final concentration=2.46M gly, 2.46M EG, 0.615M formamide, 0.615M DMSO, 0.615M PG, 0.615M methanol, 2.3M ethanol.

TABLE 2ll

| | In PBS solution | | | | | | |
|---|---|---|---|---|---|---|---|
| Treatment | Location | Recovery (%) | Age | Sex | Source | Date | Trial |
| G-EG-F-D-PG-Me—Et | Femoral | 94.00 | 54 | Female | TKA10 | Apr. 01, 2010 | 67 |
| | Femoral | 8.48 | 74 | Female | TKA20 | Apr. 21, 2010 | 67 |
| | Femoral | 54.27 | 57 | Female | TKA31c | May 07, 2010 | 67 |
| | Avg | 52.25 | | | | | |

TABLE 2mm

| | In X-VIVO solution | | | | | | |
|---|---|---|---|---|---|---|---|
| Treatment | Location | Recovery (%) | Age | Sex | Source | Date | Trial |
| G-EG-F-D-PG-Me—Et (8M) | Femoral | 25.79 | 59 | Male | TKA8 | Mar. 31, 2010 | 67 |
| | Femoral | 69.36 | 64 | Female | TKA29a | May 06, 2010 | 67 |
| | Femoral | 0.52 | 67 | Male | TKA36 | May 14, 2010 | 67 |
| | Avg | 31.89 | | | | | |

Devitrification Assessment

Grading system for visual inspection of solutions undergoing vitrification can be seen in the below table 3:

TABLE 3

| Grade | Vitrification Quality | Devitrification |
|---|---|---|
| 0 | Ice formation | Ice formation |
| 1 | Partially vitrified | Devitrified upon rewarming |
| 2 | Mostly vitrified | Devitrified upon rewarming |
| 2.5 | Vitrified and cracked | Devitrified upon rewarming |
| 3.0 | Vitrified and no cracks | Devitrified upon rewarming |
| 3.3 | Vitrified and cracked | Partially devitrified upon rewarming |
| 3.5 | Vitrified and no cracks | Partially devitrified upon rewarming |
| 3.7 | Vitrified and cracked | Some devitrification on edge upon rewarming |
| 4 | Vitrified and no cracks | Some devitrification on edge upon rewarming |
| 4.5 | Vitrified and cracked | Did not devitrify upon rewarming |
| 5 | Vitrified and no cracks | Did not devitrify upon rewarming |

The ability to vitrify is given first priority, followed by the absence of devitrification. Cracking is taken into consideration, but does not necessarily indicate that a solution is not an effective one. In one aspect of the invention, a score of 3.7 or higher is desired for a vitrification solution.

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings. Such modifications are intended to fall within the scope of the appended claims.

All publications, patents and patent applications referred to herein, or referenced in such documents are incorporated by reference in their entirety to the same extent as if each individual publication, patent or patent application was specifically and individually indicated to be incorporated by reference in its entirety. The citation of any reference herein is not an admission that such reference is available as prior art to the instant invention.

What is claimed is:

1. A method for cryopreserving articular cartilage using more than one cryopreserving agent (CPA), the method comprising:
   permeating a sample of articular cartilage with a sequence of at least two different CPAs comprising a first CPA and a second CPA, the second CPA being permeated into the sample after permeating the sample with the first CPA, to form combined CPAs having a concentration distribution within the sample;
   the concentration distribution of the combined CPAs being selected so that upon cooling of the sample, the combined CPAs vitrify and cryopreserve the sample; and
   vitrifying the sample by cooling the sample below the glass transition temperature of the permeated sample of articular cartilage in a sequence of cooling steps corresponding to the sequential addition of CPAs.

2. The method of claim 1 in which the sequence of at least two different CPAs comprises a third CPA permeated into the sample after permeating the sample with the second CPA.

3. The method of claim 2 in which the sequence of at least two different CPAs comprises a fourth CPA permeated into the sample after permeating the sample with the third CPA.

4. The method of claim 3 in which the fourth CPA is selected from the group comprising dimethyl sulfoxide, ethylene glycol, propylene glycol, glycerol.

5. The method of claim 3 in which the sequence of CPAs is D-G-PG-EG, G-EG-D-F, EG-G-D-PG, EG-G-F-D or D-G-EG-F.

6. The method of claim 2 in which the third CPA is selected from the group comprising dimethyl sulfoxide (D), ethylene glycol (EG), propylene glycol (PG), glycerol (G) and formamide (F).

7. The method of claim 1 in which the first CPA is selected from the group comprising dimethyl sulfoxide (D), ethylene glycol (EG), propylene glycol (PG), glycerol (G) and formamide (F).

8. The method of claim 1 in which the second CPA is selected from the group comprising dimethyl sulfoxide (D), ethylene glycol (EG), propylene glycol (PG), glycerol (G) and formamide (F).

9. The method of claim 1 in which the CPAs are selected from the group comprising dimethyl sulfoxide, ethylene glycol, propylene glycol, glycerol, formamide, methanol and ethanol.

10. The method of claim 1 in which the sequence of at least two different CPAs comprises five different CPAs.

11. The method of claim 1 in which the sequence of at least two different CPAs comprises six different CPAs.

12. The method of claim 1 in which the sequence of at least two different CPAs comprises seven different CPAs.

13. The method of claim 1 in which the CPAs are chosen from the group comprising dimethyl sulfoxide, ethylene glycol, propylene glycol, glycerol, formamide, methanol and ethanol.

14. The method of claim 1 in which either the first CPA or the second CPA is glycerol.

15. The method of claim 1 in which one or more of the CPAs in the sequence of CPAs are combined with chondroitin sulphate.

16. The method of claim 1 in which each succeeding CPA is permeated into the sample along with each preceding CPA.

17. The method of claim 16 in which the preceding CPA added with each succeeding CPA has a concentration substantially equal to the concentration of the preceding CPA in the sample cartilage.

18. The method of claim 1 in which one or more of the CPAs in the sequence of CPAs is combined with hyaluronic acid.

19. The method of claim 1 in which the sequence of CPAs comprises one of the given examples in Tables 2a-2ll.

20. The method of claim 1 in which the sample is from a cadaver.

\* \* \* \* \*